(12) United States Patent
Minoura et al.

(10) Patent No.: US 9,079,168 B2
(45) Date of Patent: Jul. 14, 2015

(54) PROCESS FOR PRODUCING PROPYLENE

(75) Inventors: Haruyuki Minoura, Tokyo (JP);
Yoshikazu Takamatsu, Tokyo (JP)

(73) Assignee: ASAHI KASEI CHEMICALS CORPORATION, Tokyo (JP)

(*) Notice: Subject to any disclaimer, the term of this patent is extended or adjusted under 35 U.S.C. 154(b) by 442 days.

(21) Appl. No.: 12/676,118

(22) PCT Filed: Aug. 27, 2008

(86) PCT No.: PCT/JP2008/065319
§ 371 (c)(1),
(2), (4) Date: Mar. 2, 2010

(87) PCT Pub. No.: WO2009/031445
PCT Pub. Date: Mar. 12, 2009

(65) Prior Publication Data
US 2010/0204532 A1 Aug. 12, 2010

(30) Foreign Application Priority Data
Sep. 6, 2007 (JP) ................................. 2007-231400

(51) Int. Cl.
*B01J 35/00* (2006.01)
*B01J 29/40* (2006.01)
(Continued)

(52) U.S. Cl.
CPC ............... *B01J 35/002* (2013.01); *B01J 29/40* (2013.01); *B01J 29/44* (2013.01); *B01J 37/0009* (2013.01); *B01J 37/10* (2013.01); *B01J 37/30* (2013.01); *C07C 6/04* (2013.01); *B01J 2229/36* (2013.01)

(58) Field of Classification Search
USPC ....................................................... 585/643
See application file for complete search history.

(56) References Cited

U.S. PATENT DOCUMENTS 3,960,978 A * 6/1976 Givens et al. ................. 585/531
4,021,502 A * 5/1977 Plank et al. .................... 585/533
(Continued)

FOREIGN PATENT DOCUMENTS

JP    60-166630    8/1985
JP    06-346063    12/1994
(Continued)

OTHER PUBLICATIONS

Katada, et al., "Determination of the Acidic Properties of Zeolite by Theoretical Analysis of Temperature-Programmed Desorption of Ammonia Based on Adsorption Equilibrium" in J. Phys. Chem., 1997, 101, 5969-5977-1997, month unknown.*
(Continued)

*Primary Examiner* — In Suk Bullock
*Assistant Examiner* — Ali Z Fadhel
(74) *Attorney, Agent, or Firm* — Finnegan, Henderson, Farabow, Garrett & Dunner, L.L.P.

(57) ABSTRACT

An object of the present invention is to provide a process for producing efficiently and stably propylene from a hydrocarbon raw material containing a high concentration of ethylene. The present invention discloses a process for producing propylene, comprising catalytically converting a hydrocarbon raw material containing ethylene in an amount exceeding 50% by mass with a zeolite-containing catalyst satisfying the following (1) to (3):

(1) containing of a medium pore diameter zeolite having a pore size of from 5 to 6.5 Å;
(2) a $SiO_2/Al_2O_3$ molar ratio in the medium pore diameter zeolite being from 20 to 300; and
(3) an acid amount (TPD acid amount), determined by a high-temperature desorption amount in an ammonia temperature-programmed desorption spectrum, being from 20 to 350 μmol/g-zeolite.

5 Claims, 2 Drawing Sheets

A measurement example of an ammonia temperature-programmed desorption (TPD) spectrum.
Measurement of the TPD acid amount of the H-MFI-27/SiO₂ extrusion molded body catalyst subjected to no treatment (the catalyst used in Comparative Example 1)

On the basis of the results of the waveform separation analysis, from the area of the waveform ② having the peak top thereof at a desorption temperature of 240°C or higher, the desorption amount of ammonia was found to be 222 μmol/g-catalyst, and consequently, the TPD acid amount of the catalyst was found to be 444 μmol/g-zeolite.

(51) Int. Cl.

| | | |
|---|---|---|
| *B01J 29/44* | (2006.01) | |
| *B01J 37/00* | (2006.01) | |
| *B01J 37/10* | (2006.01) | |
| *B01J 37/30* | (2006.01) | |
| *C07C 6/04* | (2006.01) | |

(56) References Cited

U.S. PATENT DOCUMENTS

| | | | |
|---|---|---|---|
| 4,150,062 A * | 4/1979 | Garwood et al. | 585/415 |
| 4,527,001 A | 7/1985 | Kaiser | |
| 4,605,807 A * | 8/1986 | Mazurek | 585/517 |
| 4,845,063 A * | 7/1989 | Chu | 502/60 |
| 4,919,896 A * | 4/1990 | Harandi et al. | 422/142 |
| 5,019,357 A * | 5/1991 | Harandi et al. | 422/140 |
| 6,388,161 B1 | 5/2002 | Dath et al. | |
| 2010/0222203 A1* | 9/2010 | Baba et al. | 502/56 |

FOREIGN PATENT DOCUMENTS

| | | |
|---|---|---|
| JP | 2001-31979 | 2/2001 |
| JP | 2006-335729 | 12/2006 |
| JP | 2006-335730 | 12/2006 |
| WO | WO 96/13331 | 5/1996 |
| WO | WO 00/10948 | 3/2000 |
| WO | WO 2007/083241 A2 | 7/2007 |

OTHER PUBLICATIONS

Database of Zeolite Structures, available on-line at http://www.iza-structure.org/databases; accessed Jan. 13, 2012).*
Sundaram, et al., "Ethylene" in Kirk-Othmer Encyclopedia of Chemical Technology, John Wiley & Sons, 2001, available on-line Apr. 16, 2001.*
Oikawa, et al. ("Highly Selective Conversion of Ethene to Propene over SAPO-34 as a Solid Acid Catalyst" in Applied Catalysis A: General 312 (2006) 181-185)—Aug. 2006.*
International Preliminary Report on Patentability dated Apr. 8, 2010 (5 pages).
International Search Report from Japanese Patent Office for International Application No. PCT/JP2008/065319, Mailed Sep. 22, 2008.
Lide, D. R. et al., "CRC Handbook of Chemistry and Physics, a Ready-Reference Book of Chemical and Physical Data," Handbook of Chemistry and Physics, CRC Press, Inc., 75$^{th}$ Edition, p. 1-15, (1994-1995).
Office Action for JP Application No. 2009-531196 dated May 2, 2012.
De Lucas, Antonio et al., "Dealumination of HZSM-5 Zeolites: Effect of Steaming on Acidity and Aromatization Activity," Applied Catalysis A: General 154 (1997) 221-240.
Niwa, Miki et al., "Measurements of Acidic Property of Zeolites by Temperature Programmed Desorption of Ammonia," Catalysis Surveys from Japan 1 (1997) 215-226.
Supplementary European Search Report for Counterpart Application No. 08828928.5 dated Dec. 27, 2011.

* cited by examiner

PROCESS FOR PRODUCING PROPYLENE

CROSS REFERENCE TO RELATED APPLICATIONS

This application is a national phase application based on PCT/JP2008/065319, filed Aug. 27, 2008, which claims the priority of Japanese Patent Application No. 2007-231400, filed Sep. 6, 2007, the content of all of which is incorporated herein by reference.

FIELD OF THE INVENTION

The present invention relates to a process for producing propylene from ethylene by using a zeolite-containing catalyst.

BACKGROUND ART

Several processes have been known which produce propylene from an olefins-containing hydrocarbon raw material by using a zeolite-containing catalyst.

Examples known as zeolite-containing catalysts for use in the production of propylene from olefins may include a catalyst in which Ag is contained in a medium pore diameter zeolite that substantially does not contain protons and a catalyst in which the $SiO_2/Al_2O_3$ molar ratio thereof falls within a range from 200 to 5000.

Although the term "olefins" covers a broad concept, the "olefins" that have hitherto been practically used as raw materials for the production of propylene are limited to the olefins having four or more carbon atoms. However, some documents describe that raw materials other than the aforementioned olefins can be used. For example, Patent document 1 describes "a method including contacting a hydrocarbon feedstock containing one or more olefinic components of $C_4$ or greater with a crystalline silicate catalyst to produce an effluent having a second composition of one or more olefinic components of $C_3$ or greater, the feedstock and the effluent having substantially the same olefin content" (claim 1), and also describes that "preferably, the ethylene comprises from 0.1 to 50% by weight of the hydrocarbon feedstock" (paragraph 28). Patent document 2 describes a process for producing propylene from ethylene and methanol and/or dimethyl ether. Patent document 3 describes a process for the interconversion of ethylene, propylene and butenes by using as a catalyst a molecular sieve such as SAPO-34.
Patent document 1: U.S. Pat. No. 6,388,161
Patent document 2: Japanese Patent Laid-Open No. 2006-335730
Patent document 3: U.S. Pat. No. 4,527,001

DISCLOSURE OF INVENTION

Problems to be Solved by the Invention

It is advantageous for cost reasons if it is possible to produce propylene from ethylene, as the case may be. As described above, there are certainly some documents which describe that propylene can be produced from ethylene-containing raw materials. The present inventors investigated the reasons why such production of propylene has, nevertheless, not yet been practically applied, and reached an idea that the reasons may be ascribable to the fact that conventional catalysts used for such production are insufficient in capability to industrialize the production of propylene from ethylene. In particular, among the conventional catalysts, some catalysts practically raise no problem when olefins having four or more carbon atoms are used as raw materials, but are too low in catalytic activity to sufficiently convert ethylene when applied as the catalysts for the reactions adopting more stable ethylene as the raw material. Actually, according to the method described in Patent document 1, only 20% by weight of the added ethylene is converted to other olefins (Patent document 1, paragraph 35). Also, in the case based on the process described in Patent document 2, the conversion ratio is at most 6 to 42%. With such low conversion ratios, it is not realistic to put the production of propylene from ethylene into practical applications, and accordingly the utilization of ethylene is restricted to such an extent that "one or more olefinic components of $C_4$ or greater" are included as main components and a small amount of ethylene is added thereto. With an exclusive focus on the enhancement of the conversion ratio, even the low activity catalyst described in Patent document 1 or 2 permits achieving an improvement of the conversion ratio by using the catalyst in a large amount. However, this way is absolutely unpractical because the selectivity is drastically degraded to decrease the yield.

On the other hand, Patent document 3 describes the process in which a conversion to propylene is conducted by using as a feedstock a mixture composed of 50% of ethylene and 50% of nitrogen; in an example therein, the conversion ratio of ethylene is found to be 86.5% in an elapsed time of 0.75 hour, but is found to be decreased down to 48.4% in an elapsed time of as short as 2 hours. Such a catalyst that is degraded in activity in a short time cannot be said to be suitable for industrial applications.

With such a background as described above, an object of the present invention is to provide a process in which propylene is produced from a hydrocarbon raw material containing ethylene in an amount exceeding 50% by mass wherein propylene is produced from ethylene in a high yield and in a stable manner.

Means for Solving the Problems

The present inventors continuously made a diligent study for the purpose of solving the above-described problems, and consequently perfected the present invention by discovering that when a catalytic conversion reaction of an ethylene-containing hydrocarbon is conducted by using a catalyst containing a specific medium pore diameter zeolite, propylene can be produced in a high yield and in a stable manner.

Specifically, the present invention provides the following process for producing propylene.

[1] A process for producing propylene, comprising catalytically converting a hydrocarbon raw material containing ethylene in an amount exceeding 50% by mass with a zeolite-containing catalyst satisfying the following (1) through (3):

(1) containing of a medium pore diameter zeolite having a pore size of from 5 to 6.5 Å;

(2) a $SiO_2/Al_2O_3$ molar ratio in the medium pore diameter zeolite being from 20 to 300; and (3) an acid amount (TPD acid amount), determined by a high-temperature desorption amount in an ammonia temperature-programmed desorption spectrum, being from 20 to 350 μmol/g-zeolite.

[2] The process for producing propylene according to item [1], wherein the zeolite-containing catalyst is heat-treated at 550° C. or higher.

[3] The process for producing propylene according to item [1] or [2], wherein the zeolite-containing catalyst is heat-treated at 300° C. or higher in the presence of water vapor.

[4] The process for producing propylene according to any one of items [1] to [3], wherein the zeolite-containing catalyst comprises at least one selected from the group consisting of the elements belonging to the group IB in the periodic table.

[5] The process for producing propylene according to any one of items [1] to [4], comprising a step in which the hydrocarbon raw material and 10% by mass or more of water based on the hydrocarbon raw material are brought into contact with the zeolite-containing catalyst.

[6] The process for producing propylene according to any one of items [1] to [5], comprising a step in which propylene is separated from the propylene-containing gas produced by the contact of the hydrocarbon raw material with the zeolite-containing catalyst, and at least part of the remaining gas is added to the hydrocarbon raw material.

ADVANTAGEOUS EFFECTS OF THE INVENTION

According to the process of the present invention, propylene can be produced in a high yield and in a stable manner from the hydrocarbon raw material containing ethylene in an amount exceeding 50% by mass, and hence the process according to the present invention is extremely advantageous for industrial implementation.

BEST MODE FOR CARRYING OUT THE INVENTION

Figure 1:
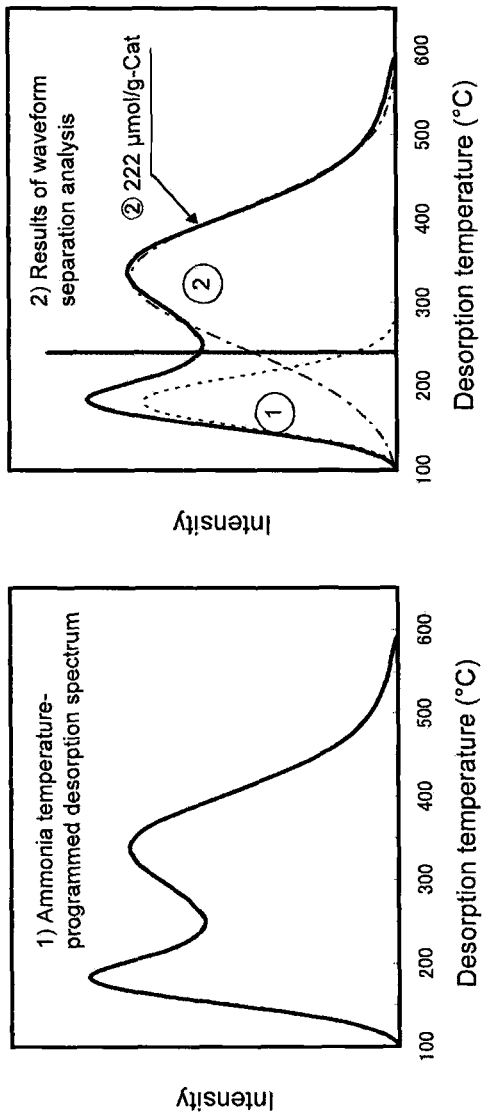
FIG. 1 shows an example of the ammonia temperature-programmed desorption spectrum of a catalyst, in particular, an example of the TPD acid amount analysis of the catalyst used in Comparative Example 1.

Hereinafter, the best mode for carrying out the present invention (hereinafter abbreviated as "the present embodiment") is described in detail. It is understood that the present invention is not limited to the following embodiment, and can be modified to be implemented within the scope of the gist thereof.

The process for producing propylene of the present embodiment is a process for producing propylene, comprising catalytically converting a hydrocarbon raw material containing ethylene in an amount exceeding 50% by mass with a zeolite-containing catalyst satisfying the following (1) through (3):

(1) containing of a medium pore diameter zeolite having a pore size of from 5 to 6.5 Å;

(2) a $SiO_2/Al_2O_3$ molar ratio in the medium pore diameter zeolite being from 20 to 300; and (3) an acid amount (TPD acid amount), determined by a high-temperature desorption amount in an ammonia temperature-programmed desorption spectrum, being from 20 to 350 μmol/g-zeolite.

The zeolite contained in the zeolite-containing catalyst in the present embodiment is a so-called "medium pore diameter zeolite" having a pore size of from 5 to 6.5 Å. The term "medium pore diameter zeolite" as used in the present embodiment means "a zeolite the pore size range of which falls in between the pores size of a small pore size zeolite typified by the A-type zeolite and the pore size of a large pore size zeolite typified by mordenite, or the X-type or Y-type zeolite," and means a zeolite which contains in the crystal structure thereof a so-called ten-membered oxygen ring.

The $SiO_2/Al_2O_3$ molar ratio of the above-described medium pore diameter zeolite falls within a range from 20 to 300. For the purpose of being capable of stably producing the present zeolite as a catalyst, the $SiO_2/Al_2O_3$ molar ratio is required to be 20 or more. When the $SiO_2/Al_2O_3$ molar ratio exceeds 300, the ethylene conversion activity is low, and the propylene selectivity is also low. When a water vapor treatment is applied to the catalyst, the activity is further decreased. The $SiO_2/Al_2O_3$ molar ratio of the zeolite can be derived by using a heretofore known method such as a method in which the zeolite is completely dissolved in an alkali aqueous solution, and the thus obtained solution is analyzed by using a method such as plasma emission spectrometry.

No particular constraint is imposed on the zeolite, as long as the zeolite falls in the category of the "medium pore diameter zeolite." Examples of the medium pore diameter zeolite may include ZSM-5 and so-called pentasil-type zeolites having a structure similar to ZSM-5, namely, zeolites such as ZSM-5, ZSM-8, ZSM-11, ZSM-12, ZSM-18, ZSM-23, ZSM-35 and ZSM-39. Examples of preferable zeolites may include a zeolite represented by the MFI structure in terms of the framework structure type in conformity with the IUPAC recommendation, and specifically include ZSM-5.

As the zeolite, there can be used a metalo-aluminosilicate in which part of the aluminum atoms constituting the zeolite framework are replaced with elements such as Ga, Fe, B and Cr and a metalosilicate in which all the aluminum atoms constituting the zeolite framework are replaced with elements such as the above-described elements. In such a case, the content of the above-described elements in the metalo-aluminosilicate or the metalosilicate is converted into the number of moles of alumina, and then the $SiO_2/Al_2O_3$ molar ratio is derived.

The method for molding the zeolite-containing catalyst in the present embodiment is not particularly limited, and may be a common method. Specifically, examples of such a method may include a method in which the catalyst component is compression molded or a method in which the catalyst component is extrusion molded, and a binder can be used for molding. The binder is not particularly limited, and for example, silica, alumina and kaolin can be used each alone or as mixtures thereof. As these binders, commercially available binders can be used. The zeolite/binder weight ratio preferably falls within a range from 10/90 to 90/10 and more preferably from 20/80 to 80/20.

For the purpose of suppressing the deterioration and improving the selectivity of the zeolite-containing catalyst in the present embodiment, the zeolite-containing catalyst may be subjected to a pretreatment, prior to being brought into contact with the hydrocarbon raw material. Preferable examples of the pretreatment may include (1) a method in which the zeolite-containing catalyst is heat-treated at temperatures of 550° C. or higher and (2) a method in which zeolite-containing catalyst is heat-treated at temperatures of 300° C. or higher in the presence of water vapor.

(1) In the case of the method in which the zeolite-containing catalyst is heated at temperatures of 550° C. or higher, heating is preferably conducted under the conditions that the temperature is set to be from 550° C. or higher to 1000° C. or lower, and air or an inert gas such as nitrogen is flowing, although the atmosphere is not particularly limited.

(2) In the case of the method in which the zeolite-containing catalyst is heated at temperatures of 300° C. or higher in the presence of water vapor, heating is conducted under the conditions that the temperature is set to be from 300° C. or higher to 900° C. or lower, a mixed gas composed of an inert gas such as nitrogen and steam is made to flow and the partial pressure of the water vapor is set to be 0.01 atm or more.

The zeolite-containing catalyst in the present embodiment is such that from the high temperature desorption amount in the ammonia temperature-programmed desorption (TPD) spectrum thereof, the acid amount (hereinafter referred to as "TPD acid amount") is derived to be from 20 to 350 µmol/g-zeolite. When the TPD acid amount of the zeolite-containing catalyst is small, the ethylene conversion activity tends to be low, and when the TPD acid amount is large, the byproduction of aromatic compounds and paraffin hydrocarbons tends to be remarkable to decrease the yield of propylene (selectivity), and additionally the activity degradation tends to be caused by coke generation. The TPD acid amount of the zeolite-containing catalyst in the present embodiment is preferably from 20 to 300 µmol/g-zeolite and more preferably from 30 to 200 µmol/g-zeolite.

The TPD acid amount is a quantity as measured in the following manner.

A catalyst as a sample is placed in a measurement cell in a temperature-programmed desorption spectrometer, the air in the measurement cell is replaced with helium gas, the temperature inside the cell is stabilized at 100° C., thereafter the interior of the cell is once subjected to a vacuum treatment, and successively ammonia gas is fed to the cell up to a pressure of 100 Torr. This condition is maintained for 30 minutes, ammonia is adsorbed to the catalyst. Thereafter, the interior of the cell is again evacuated to vacuum to let out the ammonia gas not absorbed to the catalyst, and the carrier gas is changed over to helium gas to bring the interior of the cell back to atmospheric pressure. Thereafter, the measurement cell is connected to a quadrupole mass spectrometer, the pressure inside the cell is set to be 200 Torr, and while the interior of the cell is being increased up to 600° C. in temperature at a temperature increase rate of 8.33° C./rain, the ammonia desorbed from the catalyst is detected. The pressure of the interior of the cell during the desorption is controlled so as to be maintained at approximately 200 Torr.

The obtained temperature-programmed desorption spectrum is divided by means of the waveform separation based on the Gaussian distribution, the desorption amount of ammonia is determined from the sum of the areas of the waveforms each having a peak top at a desorption temperature of 240° C. or higher, and the TPD acid amount is represented by the value (unit is µmol/g-zeolite) obtained by dividing the desorption amount of ammonia by the weight of the zeolite contained in the catalyst. The temperature of "240° C." is an indicator to be used exclusively for identification of the peak top position, but dose not mean to restrict the area calculation to the portions falling in the range of 240° C. or higher. As long as a waveform has a peak top at 240° C. or higher, the calculation of "the area of the waveform" includes the total area inclusive of the portion of a temperature other than 240° C. When two or more waveforms each have a peak top at 240° C. or higher, the area of the waveform is defined as the sum of the areas of such individual waveforms.

No particular constraint is imposed on the method for controlling the TPD acid amount of the zeolite-containing catalyst so as to fall within an intended range; examples of such a method may include: a method in which the silica/alumina molar ratio in the raw material zeolite is selected; a method in which the zeolite is subjected to ion-exchange; and a method in which the above-described heat treatment or water-vapor treatment is conducted. For example, in the ion-exchange method, the zeolite-containing catalyst can be regulated so as to have an optional TPD acid amount by adopting the way that $H^+$ or an group IB metal cation is introduced in an amount corresponding to 20 to 300 µmol/g-zeolite of the ion exchange sites of the zeolite and the other cation sites are left to be occupied by inert metal cations such as alkali metal cations and alkali earth metal cations. In the ion exchange in this case, used are hitherto well known methods such as a liquid-phase ion exchange method in which the zeolite-containing catalyst is immersed in a metal cation-containing aqueous solution and a solid phase ion exchange method which is based on a high temperature baking.

Next, the method for controlling the TPD acid amount is described with reference to the case, as an example, where the TPD acid amount is regulated by introducing $H^+$ and $Na^+$ into the cation sites by means of a liquid-phase ion exchange method. First, an H-type zeolite-containing molded body is immersed in an aqueous solution of sodium nitrate to exchange the zeolite cation sites with sodium cation. The concentration of the aqueous solution of sodium nitrate and the immersion time may be set in such a way that the H-type zeolite-containing molded body is dispersed in the aqueous solution and all the cation sites are exchanged with $Na^+$; according to need, the immersion operation may be repeated two or more times. The obtained Na-exchanged zeolite-containing molded body is filtered off, washed with water and dried, and thereafter, by introducing $H^+$ into the sites exchanged with $Na^+$, a zeolite-containing catalyst having an optional TPD acid amount can be obtained. By immersing the Na-exchanged zeolite-containing molded body in an aqueous solution of nitric acid, $H^+$ can be introduced. The concentration of the aqueous solution of nitric acid and the immersion time may be appropriately set according to the targeted TPD acid amount. For example, in a 0.05 to 0.5 N aqueous solution, the immersion is conducted for approximately 0.5 to 5 hours.

The zeolite-containing catalyst in the present embodiment may contain at least one metal element selected from the group consisting of the metal elements belonging to the group IB in the periodic table. This means that the zeolite in the catalyst contains or supports the group IB metal(s) as the state(s) of the corresponding cation(s).

It is one preferable aspect that the zeolite-containing catalyst in the present embodiment contains at least one metal selected from the group consisting of the metals belonging to the group IB in the periodic table, namely, copper, silver and gold. Among the group IB metals, copper and silver are preferable, and silver is more preferable. It is to be noted that the "periodic table" in the present embodiment means the periodic table described in CRC Handbook of Chemistry and Physics, 75th edition, by David R. Lide et al., published by CRC Press Inc., (1994-1995), pp. 1 to 15.

Examples of a method in which at least one metal element selected from the group consisting of the metal elements belonging to the group IB in the periodic table is made to be contained in the zeolite-containing catalyst in the present embodiment may include a method in which a group IB metal element is made to be contained in the zeolite, in particular, for example, a method in which a zeolite or a zeolite-containing catalyst containing no group IB metal is treated with an ion exchange method, and more specifically, a liquid phase ion exchange method and a method in which an impregnation supported catalyst is treated at high temperatures to be thereby subjected to a solid phase ion exchange treatment. In the case where a group IB metal is made to be contained in a zeolite or a zeolite-containing catalyst, it is necessary to use a salt of the group IB metal. Examples of such a salt of the group IB metal may include silver nitrate, silver acetate, silver sulfate, copper chloride, copper sulfate, copper nitrate and gold chloride. Among these, silver nitrate and copper nitrate are preferably used, and silver nitrate is more preferably used. The content of the group IB metal in the zeolite is preferably from 0.1 to 5% by mass and more preferably from 0.2 to 3% by mass. Additionally, the content can be determined by means of a method such as X-ray fluorescence analysis.

At least part of the ion exchange sites of the zeolite contained in the zeolite-containing catalyst in the present embodiment are preferably exchanged with the group IB metal cations and/or protons. Additionally, the ion exchange sites other than those exchanged with the group IB metal cations and/or protons may be exchanged with alkali metal cations, alkali earth metal cations and other metal cations.

The hydrocarbon raw material in the present embodiment contains ethylene in an amount exceeding 50% by mass. The content of ethylene in the hydrocarbon raw material is preferably 55% by mass or more and more preferably 60% by mass or more.

As the ethylene-containing hydrocarbon raw material, there can be used a material obtained by thermal decomposition and/or oxidative dehydrogenation reaction of ethane, or by dehydration reaction of ethanol. Needless to say, ethanol may be derived from biomass. Additionally, the ethylene-containing hydrocarbon raw material may contain alkanes, other olefins and the like. Specifically, examples of the alkanes may include methane, ethane, propane, butane, pentane, hexane, heptane, octane and nonane. Additionally, examples of the olefins may include propylene, butene, pentene, hexene, heptene, octene and nonene. In addition to those described above, the ethylene-containing hydrocarbon raw material may also contain: cycloalkanes such as cyclopentane, methylcyclopentane and cyclohexane; cycloolefins such as cyclopentene, methylcyclopentene and cyclohexene; and/or dienes such as cyclohexadiene, butadiene, pentadiene and cyclopentadiene and acetylenes such as acetylene, and methylacetylene. Further, the ethylene-containing hydrocarbon raw material may also contain oxygen-containing compounds such as t-butyl alcohol, methyl t-butyl ether, diethyl ether, methyl ethyl ether, dimethyl ether, ethanol and methanol.

The ethylene-containing hydrocarbon raw material may also contain water, hydrogen, nitrogen, carbon dioxide, carbon monoxide and the like.

The reaction product produced by a so-called steam cracking method of ethane in which ethane is thermally decomposed in the presence of water vapor contains, in addition to ethylene, unreacted ethane, hydrocarbons such as acetylene, water, hydrogen, carbon dioxide and carbon monoxide; however, the reaction product can be used, as it is, as a raw material.

A biomass ethanol is not particularly limited as long as the biomass ethanol is an ethanol derived from plant resources. Specific examples of biomass ethanol may include the ethanols obtained by fermentation of sugarcane and corn, and the ethanol obtained from wood resources such as waste wood, thinned wood, rice straw and agricultural products.

Propylene is separated by means of a technique such as distillation separation from the reaction product (propylene-containing gas) produced by bringing the hydrocarbon raw material into contact with the zeolite-containing catalyst, and at least part of the rest can be recycled to the reactor. The residue obtained by removing propylene from the reaction product contains an ethylene-containing low boiling point component and/or a butene-containing high boiling point component. In this case, the content of ethylene in the mixed raw material composed of the recycled component and the feedstock is a concentration exceeding 50% by mass.

Water may be fed to the reactor, together with the ethylene-containing hydrocarbon raw material from the viewpoints of improving the reaction selectivity and extending the operation life by suppressing the coke generation. When water is fed to the reactor, the ratio of water/hydrocarbon raw material is preferably 10% by mass or more, more preferably from 20 to 100% by mass and particularly preferably from 30 to 80% by mass.

The production of propylene based on the catalytic conversion reaction of ethylene is an equilibrium reaction, and the maximum yield of propylene is attained in the vicinity of the conversion ratio of ethylene of 70% in the equilibrium. Accordingly, for the purpose of efficiently obtaining propylene, the conversion ratio of ethylene preferably falls within a range from 45 to 85% and more preferably within a range from 50 to 80%. It is to be noted herein that the conversion ratio of ethylene is calculated on the basis of the following calculation formula (I).

Conversion ratio of ethylene=(ethylene concentration in the feeding flow at the reactor inlet−ethylene concentration in the discharging flow at the reactor outlet)/(ethylene concentration in the feeding flow at the reactor inlet)×100   [Formula (1)]

In this connection, no conventional technique has disclosed a method for producing propylene on the basis of a catalytic conversion in which a hydrocarbon raw material containing ethylene in an amount exceeding 50% by mass in the raw material hydrocarbon is brought into contact with a zeolite-containing catalyst. As compared to long chain olefins such as $C_4$ olefin, ethylene is low in reactivity and is hardly converted. Nevertheless, for the purpose of efficiently producing propylene, it is preferable to conduct the conversion in a high region of the conversion ratio of ethylene as described above. In other words, the zeolite-containing catalyst to be used is required to have a high activity.

The higher is made the $SiO_2/Al_2O_3$ molar ratio of the zeolite contained in the zeolite-containing catalyst in the present embodiment, the lower becomes the activity of the catalyst; accordingly, when the $SiO_2/Al_2O_3$ molar ratio is too high, the activity becomes insufficient to convert ethylene to a targeted conversion ratio. On the other hand, when the $SiO_2/Al_2O_3$ molar ratio of the zeolite contained in the zeolite-containing catalyst is made low to intend to achieve a high activation, even if a high conversion ratio of ethylene is attained, the catalyst is highly active, and consequently side reactions such as aromatization and hydrogenation tend to occur, and the deterioration of the catalyst due to the generation of coke also becomes serious.

However, surprisingly, when used the zeolite-containing catalyst in which a medium pore diameter zeolite is contained, the $SiO_2/Al_2O_3$ molar ratio of the zeolite is set to fall within a range from 20 to 300, and additionally, the TPD acid amount is controlled to be from 20 to 350 μmol/g-zeolite, even with a hydrocarbon raw material containing ethylene in an amount exceeding 50% by mass, ethylene can be converted with a high conversion ratio, propylene can be obtained with a high selectivity and the activity deterioration can also be suppressed, and hence propylene can be produced in a high yield and in a stable manner.

The reaction temperature for the production of propylene falls within a range from 300 to 650° C. and preferably within a range from 400 to 600° C. The reaction pressure falls within a range from 0.1 to 30 atm and preferably within a range from 0.5 to 10 atm.

The feeding rate of the ethylene-containing hydrocarbon raw material is from 0.1 to 20 $Hr^{-1}$ and more preferably from 0.5 to 10 $Hr^1$, in terms of the weight hourly space velocity (WHSV) with reference to the mass of the zeolite in the zeolite-containing catalyst.

No particular constraint is imposed on the reactor in which the ethylene-containing hydrocarbon raw material is made to react by being brought into contact with the zeolite-containing catalyst; as the reactor, any of a fixed bed reactor, a fluid bed reactor, a moving bed reactor and the like can be utilized.

When the zeolite-containing catalyst in the present embodiment is used for reaction over a long term, carbonaceous compounds (coke) are formed on the catalyst and the catalytic activity is decreased as the case may be. In that case, when a fixed bed reactor is used, the raw material feeding is temporarily halted, and the coke accumulated on the zeolite-containing catalyst is combusted by using an oxygen-containing gas and thus the zeolite-containing catalyst can be regenerated. Additionally, when the moving bed reactor or the fluid bed reactor is used, part of the zeolite-containing catalyst is continuously or intermittently taken out from the reactor, and the coke attached to the part of the zeolite-containing catalyst is combusted by using an oxygen-containing gas and thus the regeneration of the zeolite-containing catalyst can be conducted. The zeolite-containing catalyst after having been regenerated can be returned to the reactor. The above-described regeneration is usually conducted in air or a mixed gas composed of air and an inert gas under the condition of from 400 to 700° C.

EXAMPLES

Hereinafter, the present embodiment is described more specifically with reference to Examples, but the present embodiment is not limited only to these Examples.

It is to be noted herein that the measurement methods adopted in Examples and Comparative Examples are as follows.

(1) Measurement of the Silica/Alumina Ratio of Zeolite

To 50 g of a 5 N aqueous solution of NaOH, 0.2 g of zeolite was added. The mixture thus obtained was transferred into a stainless steel microbomb with an inner tube made of Teflon (trade mark), and the microbomb was sealed. The microbomb was retained in an oil bath for 15 to 70 hours to completely dissolve the zeolite. The obtained zeolite solution was diluted with ion-exchanged water, and the concentrations of the silicon and the aluminum in the diluted solution were measured with a plasma emission spectrometer (ICP apparatus), and from the measurement results, the silica/alumina molar ratio of the zeolite was calculated.

ICP apparatus and the measurement conditions:

| Apparatus | JOHBIN YVON (JY138 ULTRACE) manufactured by Rigaku Denki Co., Ltd. |
|---|---|
| Measurement conditions | |
| Silicon measurement wavelength | 251.60 nm |
| Aluminum measurement wavelength | 396.152 nm |
| Plasma power | 1.0 kW |
| Nebulizer gas | 0.28 L/min |
| Sheath gas | 0.3 to 0.8 L/min |
| Coolant gas | 13 L/min |

(2) Measurement of the TPD Acid Amount

The measurement was conducted by using an automatic temperature-programmed desorption spectrometer, TPD-1-Atw, manufactured by BEL Japan, Inc. in the following manner.

In a special glass cell, 100 mg of a catalyst sample was filled (when the sample was a molded body, the sample was made powdery to be filled in). While helium as the carrier gas was being fed to the cell at a flow rate of 50 cc/min, the sample was heated up to 500° C. and subjected to a heat treatment for 1 hour as a preliminary treatment, and then the sample temperature was set to be 100° C. After the sample temperature was stabilized at 100° C., the interior of the cell was subjected to a vacuum treatment (0.01 Torr). Next, ammonia gas was fed to the interior of the cell, and the pressure inside the cell was set to be 100 Torr. The sample was maintained under such condition for 30 minutes so as for ammonia to be adsorbed to the catalyst. Thereafter, the interior of the cell was again subjected to a vacuum treatment to remove the unadsorbed ammonia. The carrier gas was changed over to helium, the interior of the cell was brought back to atmospheric pressure. Thereafter, the pressure inside the cell was set so as to be maintained at 200 Torr, and while the temperature was being increased up to 600° C. at a temperature increase rate of 8.33° C./rain, the desorbed ammonia was detected with a quadrupole mass spectrometer, manufactured by ANELVA Corp., connected to the cell.

The obtained temperature-programmed desorption spectrum was divided by means of the waveform separation based on the Gaussian distribution, by using a waveform analysis software "WaveAnalysis" manufactured by BEL Japan, Inc.

On the basis of the results of the waveform separation analysis, the desorption amount of ammonia was determined from the sum of the areas of the waveforms each having a peak top at a desorption temperature of 240° C. or higher, with reference to a separately determined calibration curve, and the obtained desorption amount of ammonia was converted to a value represented in terms of the quantity per weight of zeolite (unit: μmol/g-zeolite).

Figure 2:
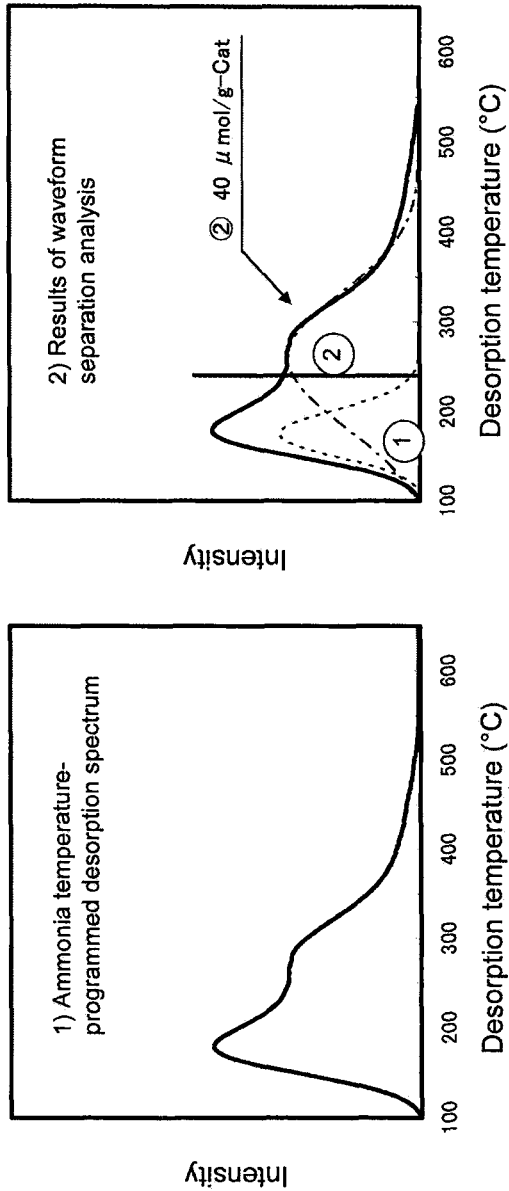
FIG. 2 shows an example of the ammonia temperature-programmed desorption spectrum of a catalyst, in particular, an example of the TPD acid amount analysis of the catalyst used in Example 7.

FIG. 1 and FIG. 2 each show an example of the temperature-programmed desorption spectrum of the catalyst used in a Comparative Example or an Example. FIG. 1 shows the calculation result of the TPD acid amount obtained in the zeolite-containing catalyst used in Comparative Example 1. As shown in 2) of FIG. 1, from the results of the waveform separation analysis, the desorption amount of ammonia was obtained on the basis of the sum of the areas of the waveforms each having a peak top at a desorption temperature of 240° C. or higher and the separately determined calibration curve; the obtained desorption amount of ammonia was converted to a value represented in terms of the quantity per weight of zeolite (unit: μmol/g-zeolite); and thus the TPD acid amount of the zeolite-containing catalyst used in Comparative Example 1 was calculated to be 444 μmol/g-zeolite.

FIG. 2 shows the calculation result of the TPD acid amount obtained in the zeolite-containing catalyst used in Example 7; on the basis of the analysis results obtained in the same manner as described above, the TPD acid amount of the zeolite-containing catalyst used in Example 7 was calculated to be 80 μmol/g-zeolite.

Example 1

An H-type ZSM-5 zeolite having a $SiO_2/Al_2O_3$ molar ratio of 30 (obtained by measuring the zeolite as completely dissolved, by means of the ICP method) was compression molded, thereafter crushed, and classified into a catalyst of 8 to 20 mesh. The obtained catalyst was filled in a quartz glass reactor of 20 mmφ in inner diameter, and was subjected to a water vapor treatment for 5 hours under the conditions of the temperature set at 650° C., a steam flow rate of 32 g/hr and a nitrogen flow rate of 10 NL/hr. The TPD acid amount of the catalyst after the water vapor treatment was found in the above-described manner to be 82 µmol/g-zeolite.

In a stainless steel reaction tube of 15 mm in inner diameter, 3.2 g of the water vapor treated catalyst was filled, and the reaction was conducted under the following conditions:

| Raw material feeding rates (flow rate converted to standard temperature & pressure condition) | ethylene nitrogen | 9.60 NL/hr 7.44 NL/hr |
|---|---|---|
| Reaction pressure | | 0.07 MPa/G |
| Reaction temperature | | 550° C. |

The reaction product was subjected to composition analysis by introducing the reaction product after a predetermined elapsed time from the start of the raw material feeding, directly from the reactor outlet into a gas chromatograph (detectors: TCD, FID). It is to be noted herein that the analysis based on gas chromatography was conducted under the following conditions.

| (Conditions for gas chromatography analysis) | |
|---|---|
| Apparatus | GC-17A, manufactured by Shimadzu Corp. |
| Column: Column SPB-1 (inner diameter 0.25 mm, length: 60 cm, film thickness: 3.0 µm) manufactured by Supelco Co., Ltd., USA | Custom Capillary |
| Sample gas amount | 1 mL (sampling line was maintained at 200 to 300° C. by heating) |
| Temperature increase program | Temperature was maintained at 40° C. for 12 minutes, then increased up to 200° C. at a rate of 5° C./min, and thereafter maintained at 200° C. for 22 minutes. |
| Split ratio | 200:1 |
| Carrier gas (nitrogen) flow rate | 120 mL/min |
| FID detector: air feeding pressure (approximately 500 mL/min); hydrogen feeding pressure | 50 kPa 60 kPa (approximately 50 mL/min) |

Measurement method: A TCD detector and an FID detector were connected in series, hydrogen and hydrocarbons having one and two carbon atoms were detected with the TCD detector and hydrocarbons having three or more carbon atoms were detected with the FID detector; after the elapsed time of 10 minutes from the start of the analysis, the detection output was changed over from TCD to FID.

While the analysis of the reaction product was being conducted appropriately, the reaction was conducted continuously for 12 hours. The results thus obtained are shown in Table 1.

Example 2

The reaction was conducted in the same manner as in Example 1 except that the reaction conditions were as follows:

| Raw material feeding rates (the concentration of water based ethylene was 50% by mass) | ethylene water | 9.60 NL/hr 6.00 g/hr |
|---|---|---|
| Reaction pressure | | 0.07 MPa/G |
| Reaction temperature | | 550° C. |

While the analysis of the reaction product was being conducted appropriately, the reaction was conducted continuously for 12 hours. The results thus obtained are shown in Table 1.

As can be seen from present Example, by conducting the conversion reaction in the concomitant presence of water, the propylene selectivity and the yield of propylene are improved.

Example 3

An H-type ZSM-5 zeolite having a $SiO_2/Al_2O_3$ molar ratio of 280 (obtained by measuring the zeolite as completely dissolved, by means of the ICP method) was compression molded, thereafter crushed, and classified into a catalyst of 8 to 20 mesh. The obtained catalyst was filled in a quartz glass reactor of 20 mmϕ in inner diameter, and was subjected to a water vapor treatment for 5 hours under the conditions of the temperature set at 650° C., a steam flow rate of 32 g/hr and a nitrogen flow rate of 10 NL/hr. The TPD acid amount of the catalyst after the water vapor treatment was found to be 44 µmol/g-zeolite.

In a stainless steel reaction tube of 15 mm in inner diameter, 5.5 g of the water vapor treated catalyst was filled, and the reaction was conducted in the same manner as in Example 2. The results thus obtained are shown in Table 1.

Example 4

The H-type ZSM-5 zeolite having a $SiO_2/Al_2O_3$ molar ratio of 280 was compression molded, thereafter crushed, and classified into a catalyst of 8 to 20 mesh.

The TPD acid amount of the obtained catalyst was found to be 96 µmol/g-zeolite.

In a stainless steel reaction tube of 15 mm in inner diameter, 1.8 g of the catalyst was filled, and the reaction was conducted under the following conditions:

| Raw material feeding rates | ethylene | 4.64 NL/hr |
|---|---|---|
| | hydrogen | 4.58 NL/hr |
| | nitrogen | 2.46 NL/hr |
| | water | 2.76 g/hr |
| Reaction pressure | | 0.07 MPa/G |
| Reaction temperature | | 550° C. |

While the analysis of the reaction product was being conducted appropriately, the reaction was conducted continuously for 6 hours.

The results of the reaction obtained at the following individual reaction times are as follows:

| Reaction time | (hr) | 1.0 | 3.5 | 6.0 |
|---|---|---|---|---|
| Conversion ratio of ethylene | (wt %) | 58.8 | 44.4 | 39.5 |
| Yield of propylene | (wt %) | 25.0 | 20.6 | 18.5 |
| Yield of C6-C8 aromatics | (wt %) | 3.9 | 1.8 | 1.3 |

Example 5

The H-type ZSM-5 zeolite having a $SiO_2/Al_2O_3$ molar ratio of 280 was kneaded with silica sol and extrusion molded. The content of the zeolite was 50% by mass. The obtained extrusion molded catalyst was dried at 120° C. for 6 hours, and thereafter baked at 700° C. for 5 hours to obtain a columnar zeolite-containing molded body catalyst of 2 mm in diameter and 3 to 5 mm in length. The obtained molded body catalyst was subjected to ion exchange under stirring in a 1 N aqueous solution of nitric acid, then washed with water, and dried at 120° C. for 5 hours.

The TPD acid amount of the obtained catalyst was found to be 49 μmol/g-catalyst, in other words corresponding to 98 μmol/g-zeolite in terms of the quantity per weight of zeolite.

In a stainless steel reaction tube of 15 mm in inner diameter, 8.5 g of the zeolite-containing catalyst was filled, and the reaction was conducted under the following conditions.

| Raw material feeding rates | ethylene | 4.64 NL/hr |
|---|---|---|
| | hydrogen | 4.58 NL/hr |
| | nitrogen | 2.46 NL/hr |
| | water | 2.76 g/hr |
| Reaction pressure | | 0.14 MPa/G |
| Reaction temperature | | 550° C. |

While the analysis of the reaction product was being conducted appropriately, the reaction was conducted continuously for 14 hours. The results thus obtained are shown in Table 2.

Example 6

A catalyst the same as that prepared in Example 5 was filled in a quartz glass reactor of 20 mmϕ in inner diameter, and was subjected to a water vapor treatment for 5 hours under the conditions of the temperature set at 650° C., a steam flow rate of 32 g/hr and a nitrogen flow rate of 10 NL/hr. The TPD acid amount of the catalyst after the water vapor treatment was found to be 21 μmol/g-catalyst, in other words corresponding to 42 μmol/g-zeolite in terms of the quantity per weight of zeolite.

In a stainless steel reaction tube of 15 mm in inner diameter, 8.5 g of the water vapor treated catalyst was filled, and the reaction was conducted in the same manner as in Example 5. The results thus obtained are shown in Table 2.

Example 7

The H-type ZSM-5 zeolite having a $SiO_2/Al_2O_3$ molar ratio of 27 was kneaded with silica sol and extrusion molded. The content of the zeolite was 50% by mass. The obtained extrusion molded catalyst was dried at 120° C. for 6 hours, and thereafter baked at 700° C. for 5 hours to obtain a columnar zeolite-containing molded body catalyst of 2 mm in diameter and 3 to 5 mm in length. The obtained molded body catalyst was subjected to ion exchange under stirring in a 1 N aqueous solution of nitric acid, then washed with water, and dried at 120° C. for 5 hours.

The TPD acid amount of the catalyst was found to be 222 μmol/g-catalyst, in other words corresponding to 444 μmol/g-zeolite in terms of the quantity per weight of zeolite.

The zeolite-containing molded body catalyst was filled in a quartz glass reactor of 20 mmϕ in inner diameter, and was subjected to a water vapor treatment for 8 hours under the conditions of the temperature set at 650° C., a steam flow rate of 32 g/hr and a nitrogen flow rate of 10 NL/hr. The TPD acid amount of the catalyst after the water vapor treatment was found to be 40 μmol/g-catalyst, in other words corresponding to 80 μmol/g-zeolite in terms of the quantity per weight of zeolite.

In a stainless steel reaction tube of 15 mm in inner diameter, 4.5 g of the obtained water vapor treated catalyst was filled, and the reaction was conducted in the same manner as in Example 5. The results thus obtained are shown in Table 3.

Example 8

A zeolite-containing molded body catalyst the same as that prepared in Example 7 was filled in a quartz glass reactor of 20 mmϕ in inner diameter, and was subjected to a water vapor treatment for 3 days under the conditions of the temperature set at 650° C., a steam flow rate of 32 g/hr and a nitrogen flow rate of 10 NL/hr. The TPD acid amount of the catalyst after the water vapor treatment was found to be 16 μmol/g-catalyst, in other words corresponding to 32 μmol/g-zeolite in terms of the quantity per weight of zeolite.

In a stainless steel reaction tube of 15 mm in inner diameter, 6 g of the obtained water vapor treated catalyst was filled, and the reaction was conducted in the same manner as in Example 5. The results thus obtained are shown in Table 3.

Example 9

A zeolite-containing molded body catalyst the same as that prepared in Example 7 was filled in a stainless steel reaction tube of 15 mm in inner diameter, and was subjected to a water vapor treatment for 3 days under the conditions of the temperature set at 350° C., a steam flow rate of 10 g/hr, a nitrogen flow rate of 11.22 NL/hr and a pressure of 0.4 MPa/G. The TPD acid amount of the catalyst after the water vapor treatment was found to be 123 μmol/g-catalyst, in other words corresponding to 246 μmol/g-zeolite in terms of the quantity unit weight of zeolite.

In a stainless steel reaction tube of 15 mm in inner diameter, 5 g of the obtained water vapor treated catalyst was filled, and the reaction was conducted in the same manner as in Example 5. The results thus obtained are shown in Table 3.

Example 10

The H-type ZSM-5 zeolite having a $SiO_2/Al_2O_3$ molar ratio of 27 was kneaded with silica sol and extrusion molded. The content of the zeolite was 50% by mass. The obtained extrusion molded catalyst was dried at 120° C. for 6 hours, and thereafter baked at 700° C. for 5 hours to obtain a columnar zeolite-containing molded body catalyst of 2 mm in diameter and 3 to 5 mm in length. The obtained molded body catalyst was subjected to ion exchange under stirring in a 1 N aqueous solution of nitric acid, then washed with water, and dried at 120° C. for 5 hours.

The H-type zeolite-containing molded body catalyst was dispersed in a 1 N aqueous solution (10 cc/g-zeolite molded body) of sodium nitrate, and an ion exchange treatment at room temperature for 1 hour was repeated three times. Then, filtration, washing with water and drying were conducted to prepare a Na-exchanged zeolite-containing molded body catalyst. This molded body catalyst was dispersed in a 0.01 N aqueous solution (10 cc/g-zeolite molded body) of silver nitrate, and was subjected to an ion exchange treatment at room temperature for 2 hours. Then, filtration, washing with water and drying were conducted to prepare a Na/Ag-exchanged zeolite-containing molded body catalyst. The content of Ag measured by fluorescent X-ray analysis was 0.57% by mass. The TPD acid amount of this catalyst was found to be 75 μmol/g-catalyst, in other words corresponding to 150 μmol/g-zeolite in terms of the quantity unit weight of zeolite.

The reaction was conducted in the same manner as in Example 7 except that the obtained Na/Ag-exchanged zeolite-containing molded body catalyst was used. The results thus obtained are shown in Table 4.

Example 11

The H-type ZSM-5 zeolite having a $SiO_2/Al_2O_3$ molar ratio of 42 was kneaded with silica sol and extrusion molded.

The content of the zeolite was 50% by mass. The obtained extrusion molded catalyst was dried at 120° C. for 6 hours, and thereafter baked at 700° C. for 5 hours to obtain a columnar zeolite-containing molded body catalyst of 2 mm in diameter and 3 to 5 mm in length. The obtained molded body catalyst was subjected to ion exchange under stirring in a 1 N aqueous solution of nitric acid, then washed with water, and dried at 120° C. for 5 hours.

The zeolite-containing molded body catalyst was filled in a quartz glass reactor of 20 mmφ in inner diameter, and was subjected to a water vapor treatment for 24 hours under the conditions of the temperature set at 650° C., a steam flow rate of 32 g/hr and a nitrogen flow rate of 10 NL/hr. The TPD acid amount of the catalyst after the water vapor treatment was found to be 22 μmol/g-catalyst, in other words corresponding to 44 μmol/g-zeolite in terms of the quantity per weight of zeolite.

In a stainless steel reaction tube of 15 mm in inner diameter, 3.7 g of the obtained water vapor treated catalyst was filled, and the reaction was conducted in the same manner as in Example 5. The results thus obtained are shown in Table 5.

Example 12

The reaction was conducted in the same manner as in Example 11 except that the raw material feeding rates were set as specified below on the basis of the assumption that butene was separated from the reaction product gas and recycled to be incorporated into the hydrocarbon raw material.

| Raw material feeding rates | ethylene | 3.95 NL/hr (85 wt %) |
| | 1-butene | 0.35 NL/hr (15 wt %) |
| | hydrogen | 4.58 NL/hr |
| | nitrogen | 2.46 NL/hr |
| | water | 2.76 g/hr |
| Reaction pressure | | 0.14 MPa/G |
| Reaction temperature | | 550° C. |

The results thus obtained are shown in Table 5. As can be seen from Examples 11 and 12, even when the butene component is recycled from the reaction product gas to be incorporated into the hydrocarbon raw material, propylene can be similarly produced in a high yield and in a stable manner.

Comparative Example 1

The reaction was conducted in the same manner as in Example 7 except that the catalyst was used without being subjected to the water vapor treatment. The TPD acid amount of the catalyst was found to be 444 μmol/g-zeolite.

While the analysis of the reaction product was being conducted appropriately, the reaction was conducted continuously for 7 hours. The results thus obtained are shown in Table 6.

As can be seen from the present Comparative Example and Example 7, even when the ZSM-5 zeolites having the same $SiO_2/Al_2O_3$ molar ratio of 27 are used, in the case where the TPD acid amount exceeds the value specified in the present invention, the selectivity is low and the activity deterioration is rapid and hence the above-described case is extremely disadvantageous for industrial implementation.

Comparative Example 2

An H-type ZSM-5 zeolite having a $SiO_2/Al_2O_3$ molar ratio of 400 (obtained by measuring the zeolite as completely dissolved, by means of the ICP method) was compression molded, thereafter crushed, and classified into a catalyst of 8 to 20 mesh. The TPD acid amount of the catalyst was found to be 86 μmol/g-zeolite.

In a stainless steel reaction tube of 15 mm in inner diameter, 8 g of the obtained catalyst was filled, and the reaction was conducted in the same manner as in Example 1. The results thus obtained are shown in Table 7.

Comparative Example 3

The H-type ZSM-5 zeolite having a $SiO_2/Al_2O_3$ molar ratio of 400 (obtained by measuring the zeolite as completely dissolved, by means of the ICP method) was compression molded, thereafter crushed, and classified into a catalyst of 8 to 20 mesh. The catalyst was filled in a quartz glass reactor of 20 mmφ in inner diameter, and was subjected to a water vapor treatment for 5 hours under the conditions of the temperature set at 650° C., a steam flow rate of 32 g/hr and a nitrogen flow rate of 10 NL/hr. The TPD acid amount of the catalyst after the water vapor treatment was found to be 26 μmol/g-zeolite.

In a stainless steel reaction tube of 15 mm in inner diameter, 8 g of the water vapor treated catalyst was filled, and the reaction was conducted in the same manner as in Example 1. The results thus obtained are shown in Table 7.

As can be seen from Comparative Examples 2 and 3, the zeolite exceeding the $SiO_2/Al_2O_3$ molar ratio specified in the present invention is low in activity and also in selectivity even when used as untreated for the reaction, and further decreased in activity when subjected to a water vapor treatment for the purpose of improving the selectivity.

Comparative Example 4

A SAPO 34 having a molar ratio Si/Al/P of 2/12.6/9.9 was compression molded, and thereafter crushed and classified into a catalyst of 8 to 20 mesh. In a stainless steel reaction tube of 15 mm in inner diameter, 10 g of the catalyst was filled, and the reaction was conducted under the following conditions:

| Raw material feeding rates (flow rate converted to standard temperature & pressure condition) | ethylene | 4.80 NL/hr |
| | nitrogen | 3.72 NL/hr |
| Reaction pressure | | 0.07 MPa/G |
| Reaction temperature | | 400° C. |

The results of the reaction obtained at the following individual reaction times are as follows:

| Reaction time | (hr) | 0.5 | 2.0 | 4.0 |
| Conversion ratio of ethylene | (wt %) | 57.8 | 12.2 | 2.8 |
| Yield of Propylene | (wt %) | 39.1 | 9.0 | 1.6 |

The SAPO 34 catalyst system attains a high selectivity, but is low in activity; the SAPO 34 catalyst system is needed in a large amount, and the activity deterioration has been found remarkable. Accordingly, it should be stated that the industrial implementation of such a catalyst is extremely disadvantageous.

TABLE 1

|  |  | Example 1 | | | Example 2 | | | Example 3 | | |
|---|---|---|---|---|---|---|---|---|---|---|
|  |  | Catalyst | | | | | | | | |
|  |  | H-MFI-30 Water vapor treatment at 650° C. for 5 hours | | | H-MFI-30 Water vapor treatment at 650° C. for 5 hours | | | H-MFI-280 Water vapor treatment at 650° C. for 5 hours | | |
| TPD acid amount | μmol/g-Zeolite | 82 | | | 82 | | | 44 | | |
| Catalyst amount | g | 3.00 | | | 3.00 | | | 5.50 | | |
| Ethylene | NL/hr | 9.60 | | | 9.60 | | | 9.60 | | |
| Hydrogen | NL/hr | | | | | | | | | |
| Nitrogen | NL/hr | 7.44 | | | | | | | | |
| Water | g/hr | | | | 6.00 | | | 6.00 | | |
| Pressure | MPa/G | 0.07 | | | 0.07 | | | 0.07 | | |
| Temperature | ° C. | 550 | | | 550 | | | 550 | | |
| Reaction time | Hr | 3.0 | 7.0 | 12.0 | 3.0 | 8.0 | 12.0 | 1.0 | 5.0 | 8.0 |
| Conversion ratio of ethylene | wt % | 70.4 | 65.4 | 61.1 | 79.3 | 79.1 | 77.7 | 66.7 | 58.3 | 51.6 |
| Yield of propylene | wt % | 24.2 | 24.1 | 23.1 | 25.2 | 26.2 | 26.5 | 27.6 | 25.4 | 23.2 |
| Yield of C6 to C8 aromatics | wt % | 10.5 | 8.5 | 7.1 | 7.9 | 7.9 | 7.2 | 4.0 | 2.6 | 1.8 |

TABLE 2

|  |  | Example 5 | | | | Example 6 | | | |
|---|---|---|---|---|---|---|---|---|---|
|  |  | Catalyst | | | | | | | |
|  |  | H-MFI-280/SiO2 | | | | H-MFI-280/SiO2 Water vapor treatment at 650° C. for 5 hours | | | |
| TPD acid amount | μmol/g-Zeolite | 98 | | | | 42 | | | |
| Catalyst amount | g | 8.50 | | | | 8.50 | | | |
| Ethylene | NL/hr | 4.64 | | | | 4.64 | | | |
| Hydrogen | NL/hr | 4.58 | | | | 4.58 | | | |
| Nitrogen | NL/hr | 2.46 | | | | 2.46 | | | |
| Water | g/hr | 2.76 | | | | 2.76 | | | |
| Pressure | MPa/G | 0.14 | | | | 0.14 | | | |
| Temperature | ° C. | 550 | | | | 550 | | | |
| Reaction time | Hr | 2.0 | 6.0 | 10.0 | 14.0 | 2.0 | 6.0 | 10.0 | 14.0 |
| Conversion ratio of ethylene | wt % | 85.8 | 82.4 | 80.5 | 78.8 | 77.9 | 72.6 | 67.4 | 61.7 |
| Yield of propylene | wt % | 16.0 | 20.6 | 22.8 | 23.4 | 24.9 | 25.9 | 25.9 | 24.8 |
| Yield of C6 to C8 aromatics | wt % | 18.4 | 13.9 | 11.7 | 10.3 | 7.7 | 4.8 | 3.7 | 2.7 |

TABLE 3

|  |  | Example 7 | | | Example 8 | | | Example 9 | | |
|---|---|---|---|---|---|---|---|---|---|---|
|  |  | Catalyst | | | | | | | | |
|  |  | H-MFI-27/SiO2 Water vapor treatment at 650° C. for 8 hours | | | H-MFI-27/SiO2 Water vapor treatment at 650° C. for 72 hours | | | H-MFI-27/SiO2 Water vapor treatment at 350° C. for 72 hours | | |
| TPD acid amount | μmol/g-Zeolite | 80 | | | 32 | | | 246 | | |
| Catalyst amount | g | 4.50 | | | 6.00 | | | 5.00 | | |
| Ethylene | NL/hr | 4.64 | | | 4.64 | | | 4.64 | | |
| Hydrogen | NL/hr | 4.58 | | | 4.58 | | | 4.58 | | |
| Nitrogen | NL/hr | 2.46 | | | 2.46 | | | 2.46 | | |
| Water | g/hr | 2.76 | | | 2.76 | | | 2.76 | | |
| Pressure | MPa/G | 0.14 | | | 0.14 | | | 0.14 | | |
| Temperature | ° C. | 550 | | | 550 | | | 550 | | |
| Reaction time | Hr | 2.0 | 12.0 | 20.0 | 2.0 | 10.0 | 16.0 | 2.0 | 5.0 | 11.0 |
| Conversion ratio of ethylene | wt % | 81.9 | 75.5 | 70.9 | 74.7 | 70.3 | 69.3 | 79.3 | 76.1 | 71.6 |
| Yield of propylene | wt % | 22.3 | 26.4 | 26.9 | 28.3 | 28.9 | 28.3 | 24.1 | 25.4 | 26.3 |
| Yield of C6 to C8 aromatics | wt % | 13.9 | 8.5 | 6.2 | 6.3 | 4.4 | 4.1 | 11.3 | 10.1 | 7.9 |

TABLE 4

|  |  | Example 10<br>Catalyst<br>Ag/Na-MFI-27/SiO2 |  |  |  |
|---|---|---|---|---|---|
| TPD acid amount | μmol/g-Zeolite | 150 | | | |
| Catalyst amount | g | 4.50 | | | |
| Ethylene | NL/hr | 4.64 | | | |
| Hydrogen | NL/hr | 4.58 | | | |
| Nitrogen | NL/hr | 2.46 | | | |
| Water | g/hr | 2.76 | | | |
| Pressure | MPa/G | 0.14 | | | |
| Temperature | °C. | 550 | | | |
| Reaction time | Hr | 2.0 | 7.0 | 10.0 | 16.0 |
| Conversion ratio of ethylene | wt % | 83.6 | 74.2 | 69.8 | 59.5 |
| Yield of propylene | wt % | 17.8 | 25.4 | 25.8 | 24.7 |
| Yield of C6 to C8 aromatics | wt % | 19.1 | 9.7 | 7.0 | 5.2 |

TABLE 5

|  |  |  | Example 11 | | | Example 12 | | |
|---|---|---|---|---|---|---|---|---|
|  |  |  | Catalyst | | | | | |
|  |  |  | H-MFI-42/SiO2<br>Water vapor treatment at<br>650° C. for 24 hours | | | H-MFI-42/SiO2<br>Water vapor treatment at<br>650° C. for 24 hours | | |
| TPD acid amount | | μmol/g-Zeolite | 44 | | | 44 | | |
| Catalyst amount | | g | 3.70 | | | 3.70 | | |
| Ethylene | | NL/hr | 4.64 | | | 3.95 | | |
| 1-Butene | | NL/hr | | | | 0.35 | | |
| Hydrogen | | NL/hr | 4.58 | | | 4.58 | | |
| Nitrogen | | NL/hr | 2.46 | | | 2.46 | | |
| Water | | g/hr | 2.76 | | | 2.76 | | |
| Pressure | | MPa/G | 0.14 | | | 0.14 | | |
| Temperature | | °C. | 550 | | | 550 | | |
| Reaction time | | Hr | 2.0 | 6.0 | 12.0 | 2.0 | 4.0 | 8.0 |
| Inlet | Hydrogen | wt % | 6.6 | | | 6.6 | | |
|  | Ethylene | wt % | 93.4 | | | 79.4 | | |
|  | Butene | wt % | 0.0 | | | 14.0 | | |
| Outlet composition | Ethylene | wt % | 30.6 | 31.1 | 32.8 | 28.4 | 29.7 | 30.3 |
|  | Propylene | wt % | 25.6 | 25.2 | 25.2 | 24.7 | 26.3 | 26.4 |
|  | Butene | wt % | 13.7 | 13.5 | 13.5 | 13.9 | 14.3 | 14.7 |
|  | C6 to C8 aromatics | wt % | 4.0 | 3.7 | 3.3 | 5.7 | 4.3 | 3.9 |
| Conversion ratio of ethylene | | wt % | 67.3 | 66.7 | 64.9 | 64.2 | 62.6 | 61.9 |
| Yield of propylene | | wt % | 27.4 | 27.0 | 27.0 | 31.1 | 33.0 | 33.3 |

TABLE 6

|  |  | Comparative Example 1<br>Catalyst<br>H-MFI-27/SiO2 | | | |
|---|---|---|---|---|---|
| TPD acid amount | μmol/g-Zeolite | 444 | | | |
| Catalyst amount | g | 4.50 | | | |
| Ethylene | NL/hr | 4.64 | | | |
| Hydrogen | NL/hr | 4.58 | | | |
| Nitrogen | NL/hr | 2.46 | | | |
| Water | g/hr | 2.76 | | | |
| Pressure | MPa/G | 0.14 | | | |
| Temperature | °C. | 550 | | | |
| Reaction time | Hr | 1.0 | 3.0 | 5.0 | 7.0 |
| Conversion ratio of ethylene | wt % | 89.6 | 80.2 | 60.2 | 41.8 |
| Yield of propylene | wt % | 11.6 | 20.4 | 23.1 | 18.2 |
| Yield of C6 to C8 aromatics | wt % | 25.7 | 15.1 | 6.5 | 3.3 |

TABLE 7

|  |  | Comparative Example 2 | Comparative Example 3 |
|---|---|---|---|
|  |  | Catalyst | |
|  |  | H-MFI-400 | H-MFI-400<br>Water vapor treatment at<br>650° C. for 5 hours |
| TPD acid amount | μmol/g-Zeolite | 86 | 26 |
| Catalyst amount | g | 8.00 | 8.00 |

TABLE 7-continued

|  |  | Comparative Example 2 | | | Comparative Example 3 | |
|---|---|---|---|---|---|---|
|  |  | Catalyst | | | | |
|  |  | H-MFI-400 | | | H-MFI-400 Water vapor treatment at 650° C. for 5 hours | |
| Ethylene | NL/hr | 9.60 | | | 9.60 | |
| Nitrogen | NL/hr | 7.44 | | | 7.44 | |
| Pressure | MPa/G | 0.07 | | | 0.07 | |
| Temperature | ° C. | 550 | | | 550 | |
| Reaction time | Hr | 1.0 | 5.0 | 10.0 | 1.0 | 3.0 |
| Conversion ratio of ethylene | wt % | 62.7 | 49.0 | 42.0 | 3.3 | 3.3 |
| Yield of propylene | wt % | 21.3 | 18.0 | 16.3 | 1.0 | 1.0 |

The present application is based on Japanese Patent Application (Patent Application No. 2007-231400) filed on Sep. 6, 2007, and the contents thereof are incorporated herein by reference.

Industrial Applicability

The process for producing propylene according to the present invention permits efficiently and stably producing propylene from a hydrocarbon raw material containing ethylene in an amount exceeding 50% by mass, and is also useful as an industrial production process from the viewpoint of the diversity of the raw materials for producing propylene.

What is claimed is:

1. A process for producing propylene, comprising catalytically converting at a temperature within a range of 400 to 600° C. a hydrocarbon raw material containing ethylene in an amount exceeding 50% by mass to a propylene-containing gas with a zeolite-containing catalyst satisfying the following (1) through (4):

(1) containing of a medium pore diameter zeolite having a pore size of from 5 to 6.5 Å;

(2) a $SiO_2/Al_2O_3$ molar ratio in the medium pore diameter zeolite being from 20 to 300;

(3) an acid amount (TPD acid amount), determined by a high-temperature desorption amount in an ammonia temperature-programmed desorption spectrum, being from 20 to 350 μmol/g-zeolite, and (4) wherein the zeolite-containing catalyst is heat-treated at 300° C. or higher in the presence of water vapor, wherein the conversion rate of ethylene is within the range from 50 -85% and wherein the yield of propylene is greater than 20.6 weight %.

2. The process for producing propylene according to claim 1, wherein the zeolite-containing catalyst is heat-treated at 550° C. or higher.

3. The process for producing propylene according to claim 1 or 2, wherein the zeolite-containing catalyst comprises at least one element selected from the group consisting of the elements belonging to the group IB in the periodic table.

4. The process for producing propylene according to claim 1 or 2, comprising a step in which the hydrocarbon raw material and 10% by mass or more of water based on the hydrocarbon raw material are brought into contact with the zeolite-containing catalyst.

5. The process for producing propylene according to claim 1 or 2, comprising a step in which propylene is separated from the propylene-containing gas produced by the contact of the hydrocarbon raw material with the zeolite-containing catalyst, and at least part of the remaining gas is added to the hydrocarbon raw material.

* * * * *